US007440788B2

(12) United States Patent
Jenkins et al.

(10) Patent No.: US 7,440,788 B2
(45) Date of Patent: Oct. 21, 2008

(54) ORAL HEALTH MEASUREMENT CLAMPING PROBE, SYSTEM, AND METHOD

(75) Inventors: Julian Jenkins, Santa Cruz, CA (US);
Tim Robins, Capitola, CA (US); Gareth Feighery, Santa Cruz, CA (US); Andre Grouwstra, Morgan Hill, CA (US); Essam Badawi, Scotts Valley, CA (US); Kelvyn Evans, Walkoloa, HI (US)

(73) Assignee: Kelvyn Enterprises, Inc., Waikoloa, HI (US)

( * ) Notice: Subject to any disclaimer, the term of this patent is extended or adjusted under 35 U.S.C. 154(b) by 894 days.

(21) Appl. No.: 10/928,631

(22) Filed: Aug. 26, 2004

(65) Prior Publication Data
US 2006/0047190 A1     Mar. 2, 2006

(51) Int. Cl.
*A61B 5/1455* (2006.01)
(52) U.S. Cl. .................. 600/344; 600/322; 600/340
(58) Field of Classification Search ............... 600/322, 600/323, 340, 344
See application file for complete search history.

(56) References Cited

U.S. PATENT DOCUMENTS

| 3,799,672 | A |   | 3/1974 | Vurek |         |
|-----------|---|---|--------|--------|--------|
| 4,167,331 | A |   | 9/1979 | Nielsen |        |
| 4,564,355 | A |   | 1/1986 | Traiger et al. |  |
| 4,685,464 | A |   | 8/1987 | Goldberger et al. | |
| 4,824,242 | A |   | 4/1989 | Frick et al. |     |
| 4,836,206 | A |   | 6/1989 | Maxwell et al. |   |
| 4,890,619 | A | * | 1/1990 | Hatschek | 600/323 |
| 5,040,539 | A |   | 8/1991 | Schmitt et al. |   |
| 5,090,410 | A | * | 2/1992 | Saper et al. | 602/41 |
| 5,209,230 | A | * | 5/1993 | Swedlow et al. | 600/322 |

(Continued)

FOREIGN PATENT DOCUMENTS

DE     19649689     6/1998

(Continued)

OTHER PUBLICATIONS

Busch et al., "Nonin Onyx Pulse Oximeter", AVweb [online] Dec. 6, 1999, retrieved from the Internet: <URL: http://www.avweb.com/cgi-bin/im.display.printable:client.id=avweb&story.id=181936> on Apr. 7, 2004.

(Continued)

*Primary Examiner*—Eric F Winakur
*Assistant Examiner*—Etsub D Berhanu
(74) *Attorney, Agent, or Firm*—Central Coast Patent Agency, Inc

(57) ABSTRACT

Devices, systems, and methods determine the health of oral objects by providing objective measurements using a detachable probe body. The detachable probe body may isolate reusable system components (including an electromagnetic signal detection, signal transmission, energy generation, and or energy transmitting components) from the oral cavity, optionally by encasing at least a portion of one or more of these components in a sheath or the like. A window of the probe body maintains sterile isolation and transmits electromagnetic energy to and or signals from the oral object. Accuracy can be enhanced by a clamp or other structure for engaging a surface of the oral object so as to maintain a fixed alignment between the signal receiver and the oral object.

51 Claims, 5 Drawing Sheets

U.S. PATENT DOCUMENTS

| | | | |
|---|---|---|---|
| 5,259,761 | A | 11/1993 | Schnettler et al. |
| 5,630,413 | A | 5/1997 | Thomas et al. |
| 5,755,226 | A * | 5/1998 | Carim et al. ............ 600/323 |
| 5,921,776 | A | 7/1999 | Hielbrumm |
| 6,095,974 | A | 8/2000 | Shemwell et al. |
| 6,253,097 | B1 * | 6/2001 | Aronow et al. ............ 600/310 |
| 6,430,422 | B1 * | 8/2002 | Kimura ............ 600/310 |
| 6,501,974 | B2 | 12/2002 | Huiku |
| 6,519,486 | B1 | 2/2003 | Edgar, Jr. et al. |
| 6,626,838 | B2 | 9/2003 | Doten et al. |
| 6,638,219 | B1 | 10/2003 | Asch et al. |
| 6,684,090 | B2 | 1/2004 | Ali et al. |
| 2002/0012897 | A1 | 1/2002 | Tingley et al. |
| 2004/0034293 | A1 | 2/2004 | Kimball |

FOREIGN PATENT DOCUMENTS

| | | |
|---|---|---|
| WO | WO 99/52420 | 10/1999 |
| WO | WO 02/100257 | 12/2002 |
| WO | WO 03/039340 | 5/2003 |

OTHER PUBLICATIONS

Nellcor, CapnoProbe Sublingual System [online] as downloaded from the Internet: <URL: http://www.nellcor.com/prod/product.aspx?S1=SUB&ID=248> on Aug. 30, 2004.

Moor Instruments, Laser Doppler Monitors [online] retrieved from Internet: <URL: http://www.moor.co.uk/prod_laser_doppler_monitors.htm> on Jul. 30, 2004.

Moor Instruments floLAB, Laser Doppler Blood Flow Monitor, Technical Manual, Moor Instruments Limited, Devon England Dec. 12, 1996.

Munshi et al. "Pulse Oximetry: A Diagnostic Instrument In Pulpal Vitality Testing", *The Journal of Clinical Pediatric Dentistry* vol. 26, No. 2, 2002.

O'Neil, "Detection and Measurement of Sublingual CO2", Reference note, Sublingual Carbon Dioxide Note No. 1, Nellcor Puritan Bennett 2002.

Perimed AB, "Applications Using the Periflux" [online], retrieved from from the Internet: <URL: http://www.perimed.se/p_Applications/Periflux.htm> on Jul. 30, 2004.

Samraj et al. "Recent Advances In Pulp Vitality Testing", Endontology, vol. 15 Issue 1, Jun. 2003, pp. 14-19.

Serov et al. "New Generation of Optoelectronic Integrated Probes for Laser Doppler Blood Flowmetry", Biophysical Techniques Group, Faculty of Applied Physics, Mesa Research Institute.

Vasamed, Developer of CapnoProbe Sublingual (SL) System, [online] Reports Recall by Nellcor, Aug. 27, 2000 retrieved from the Internet: <URL: http://_www.biotechfind.com/news/news-VASAMED-3755.htm> on Aug. 30, 2004.

* cited by examiner

ORAL HEALTH MEASUREMENT CLAMPING PROBE, SYSTEM, AND METHOD

BACKGROUND OF THE INVENTION

The present invention generally provides improved devices, systems, and methods for evaluating tissues, materials, and/or fluids within the oral cavity. In many embodiments, the invention provides improved devices, systems, and methods for determining tooth vitality (or other health characteristics of other oral objects), often through the use of a detachable probe body which allows transmission of electromagnetic signals while protecting other system components from contamination. The probe body may be disposable or sterilizable.

Diagnosing the health of a particular tooth can be a challenge. Patients may (or may not) experience tooth pain for a variety of reasons. Techniques now employed to detect the health or vitality of a tooth, and particularly of the dental pulp within a tooth, are quite subjective. As a result, dentists may perform inappropriate treatments for a tooth, in some cases without resolving or eliminating the real source of problem(s).

Techniques commonly employed to detect dental pulp vitality often rely on application of a stimulus to the tooth. The dentist may evaluate a patient's subjective response to the stimulus, in part to determine if the pulp has deteriorated so much that it must be enervated. The stimulus may include thermal (cold or heat), mechanical, and/or electrical energy applied to the tooth under examination, with the dentist asking the patient whether he or she feels any sensation.

Unfortunately, patients are often in pain when they seek treatment, and the sensations resulting from such stimuli can be intensely unpleasant to the patient. Moreover, the mere ability to sense stimulation applied to a particular tooth may not mean that the pulp within that tooth (and its nerves) remain healthy (and vice versa), and both the patient's subjective reaction to the stimuli and the dentist's subjective ability to interpret the patient's response may play a role in the evaluation. False positive indications of successful stimulation may result, for example, from indirectly stimulating surrounding tissues or nearby oral objects. Tooth stimulation examinations may also provide little information regarding gradual changes underway in tooth vitality. As a result of the limitations on clinical techniques for accurately determining tooth vitality, patients may have the wrong tooth extracted, removing a viable tooth while the original source of the problem remains, or patients may be subjected to other forms of misplaced treatment.

A variety of improvements have been suggested for more accurately and more objectively measuring tooth vitality. Studies have proposed applying pulse oximetry and laser Doppler flowmetry to determine the integrity of the pulp underlying a tooth. These proposals have indicated that it may be possible to detect blood oxygenation and/or flow using, for example, the changes in light absorption passing through a tooth, the shift in light frequency returned back from a tooth, or the like. Unfortunately, these proposals have largely relied upon blood measurement systems intended for use in other environments. These environments differ significantly from a practicing dentist's examination room, and the existing blood measurement systems often have costs which are untenable for most dentists. As a result, despite the theoretical benefits that may be available, prior proposals for improved tooth vitality measurements have not found widespread application among practicing dentists.

In light of the above, it would be advantageous to provide improved devices, systems, and methods for measuring and/or determining tooth vitality. It would be particularly advantageous if these improvements made it practical to implement objective tooth vitality detection and measurements performed by practicing dentists on their patients. It would be particularly advantageous if these improved techniques enhanced tooth vitality measurement accuracy and objectivity using simple methods and structures suitable for use by a dentist, hygienist, or the like in the dental examination room.

BRIEF SUMMARY OF THE INVENTION

The present invention generally provides improved devices, systems, and methods for determining the health of oral objects within the oral cavity. The invention may, for example, help provide practical objective measurements of tooth vitality and the like. A variety of other oral object health characteristic measurements might also benefit from these improved (and often more objective) techniques. Oral objects for evaluation might include teeth, gums, the tongue, and/or the like. Along with oxygenation and/or other characteristics of blood and its flow within an oral object, desirable characteristics to be measured may include the presence or absence of materials, chemicals, biomaterials, bacteria, materials absorbed or secreted by bacteria, and the like.

In a first embodiment, the invention provides a detachable probe body with use with an oral health measurement system for oral health measurements of an oral object within a mouth of a patient. The mouth has oral surfaces, and the health measurement system has reusable components including an electromagnetic signal receiver coupled to a processor evaluating a health-related characteristic of the mouth from an electromagnetic signal. The probe body comprises window capable of transmitting the electromagnetic signal from the oral object to the signal receiver. A casing extends from the window, the casing and window together defining an opening for receiving the signal receiver so as to provide isolation of the reusable components from the mouth. At least one probe surface is oriented to engage one or more oral surfaces so as to maintain alignment between the signal receiver and the oral object.

The at least one probe surface region will often comprise a first probe surface region and a second probe surface region. The probe may receive the oral object with the first and second probe surface regions. The probe body will often comprise a first probe body portion having the first probe surface region and a second probe body portion having the second probe surface region, the second body portion movable relative to the first body portion. A biasing structure may urge the first probe surface region toward the second probe surface region when the oral object is at a desired position therebetween so as to accommodate a range of differing oral object sizes. For example, the first body portion may slidingly receive the second portion with the biasing structure comprising a spring urging the second region toward the first region. In some embodiments, a ratchet may couple the first portion to the second portion so as to allow the biasing structure to decrease separation between the first surface region and the second surface region. The ratchet may inhibit motion of the second surface region away from the first surface region. Such a ratchet may be used with or without a biasing mechanism, for example, by relying the dentist to move the two body portions together.

Optionally, a deformable material will define at least one of the first body portion, the second body portion, and an intermediate portion coupling the first and second body portions.

The deformable material may, for example, bias the probe surface regions towards each other. The intermediate portion may comprise a resilient spring, a polymer structure such as a soft plastic which can be bent while pressing the probe body onto a tooth, and then hold to the tooth due to the force of the resilient polymer trying to resume its original shape, or the like. Similar structures may be used to clamp a probe body to the gums, tongue, or other oral objects. The deformable material may optionally define at least one of the probe surface regions, and may be sufficiently soft so as to deform against the oral object when a dentist manually applies pressure. In some embodiments, the first probe body portion may move toward the second probe body portion when a pressure is applied with an orientation lateral relative to the movement. For example the probe body may be configured so as to induce the movement of the probe body portion and engage opposed surfaces of at least one tooth when a patient bites the probe body.

Optionally, the at least one probe surface may be defined by a material that deforms and introduces sufficient friction so as to temporarily affix the probe body relative to the oral object. Such deformable materials may be sufficiently soft so as to deform against the oral object when a dentist manually applies pressure. Suitable materials may include Thixatropic gels, and may be sufficient to hold the probe in place with no further pressure.

The reusable components of the measurement system may include a transmission medium or a wireless system. The case may fittingly receive the signal receiver to a predetermined position within the opening, and the casing may comprise a sheath receiving at least a portion of the transmission medium or the wireless system so as to maintain sterile separation between the reusable components in the mouth. Where the transmission medium comprises an optical waveguide, the signal receiver may comprise a distal end of the optical waveguide, and the sheath may distally receive the waveguide. Optionally, a mirror may be disposed along an optical path between the window and the end of the optical waveguide. A joint may couple the sheath to an oral object receiving portion of the casing so as to allow movement therebetween. More generally, the probe body may include a joint coupling at least a portion of the casing to the at least one probe surface.

In some embodiments, the transmission medium may include an electrical conductor and the signal receiver may comprise a light detector circuit. The sheath can receive a portion of the conductor adjacent the light detector circuit. The signal receiver of the oral health measurement system may be coupled to an electromagnetic source of the oral health measurement system. The casing may receive the signal receiver and at least a portion of the electromagnetic source therein.

The casing may have a feature for engaging a surface of the oral health measurement system to position the signal receiver relative to the casing. The casing may frangible or permanent deformable adjacent the feature when the signal receiver is removed from the casing so as to inhibit reuse of the probe body. At least one material of the probe body may be difficult to sterilize, with the probe body often comprising a disposable product. In some embodiments, at least an outer surface of the probe body may be sterilizable.

The oral health measurement system may have a source of visible or non-visible light energy, and another window may be provided in the probe body with or without another casing for receiving at least a portion of the energy source of the oral health measurement system. The visible or non-visible light energy may be directed toward the oral object from the other window.

The oral health measurement system may have a source of visible or non-visible light energy coupled to a transmission medium. The transmission medium may also direct the signal from the signal receiver to the processor. The signal receiver may comprise an integrated signal receiver/energy transmitter. The opening of the probe body may removably receive at least a portion of the transmission medium adjacent the integrated signal receiver/energy transmitter. Optionally, a reflective surface may be provided in the probe body with oral object being disposed between the window and the reflector when the window is oriented to transmit the energy toward the oral object. The reflector may help direct energy which has passed through the oral object back toward the window, and hence, to the integrated signal receiver/energy transmitter.

In another aspect, the invention provides a detachable probe body for use with a blood measurement system for tooth vitality measurements of a tooth within a mouth of a patient. The mouth has oral surfaces, and the blood measurement system may have reusable components including a light signal receiver coupled to a processor for evaluating a characteristic of blood from an electromagnetic signal. The probe body may comprise a window capable of transmitting the light signal from the tooth to the signal receiver. A casing may extend from the window. The casing and window together can define an opening for receiving the signal receiver and at least a portion of the signal transmitter so as to provide isolation of the reusable components from the mouth. At least one surface may be oriented to engage one or more oral surfaces so as to maintain alignment between the signal receiver and the tooth.

Along with tooth vitality measurements based on blood characteristics, the probe body may be useful for obtaining a variety of oral health measurements. The measurements may make use of pulse oximetry, spectrophotometry, laser Doppler, and the like, and may measure health characteristics of gums, the tongue, and one or more teeth. The probe body may receive the tooth with first and second surface regions, and may include a biasing structure urging the surface regions towards one another when a tooth is therebetween so as to accommodate a range of differing teeth. The surface regions of the surface body may be disposed on associated probe body portions, with a first portion slidingly engaging and being urged toward the second portion, for example, when the patient bites the probe body. Optionally, the at least one surface may be defined by a material that deforms so as to temporarily affix the probe body relative to the tooth. The material may be deformed by the dentist manually pressing the probe body against the tooth, by having the patient bite on the probe body, or the like.

In many embodiments, the casing will fittingly receive the signal receiver to a predetermined position within the opening. The blood measurement system may include an optical waveguide, and the signal receiver may include a distal end of the optical waveguide, with the opening distally receiving the waveguide. The blood flow measurement system may include an electrical conductor and the signal receiver may comprise a light detector circuit, with the opening receiving the light detector circuit and at least a portion of the conductor adjacent the light detector circuit. Still further options are possible, including making use of a blood flow measurement system that includes a light detector circuit powered by a battery or the like and providing telemetry of signals from the tooth using a wireless transmitter with the opening of the probe body receiving the light detector circuit, battery (or other circuit power source), and wireless transmitter.

A feature of the casing may engage a surface of the blood measurement system to position the signal receiver relative to the casing and/or window. The casing may be frangible or permanently deformable adjacent the feature when the signal receiver is removed from the casing so as to inhibit reuse of the probe body. In other embodiments, the casing may be sterilizable and reusable.

Blood measurement system may have a light energy source and an energy transmission medium. Another window and another casing of the probe body may define another window for, receiving the energy source and at least a portion of the energy transmission medium. In some embodiments, the blood measurement system will have a light energy source and an energy transmission medium for directing energy to the tooth, but the energy transmission medium will also direct the signal from the signal receiver to the processor. Optionally, the signal receiver may comprise an integrated signal receiver/energy transmitter. Hence, the opening of the probe body may receive at least a portion of the transmission medium adjacent the integrated signal receiver/energy transmitter, with both the light energy from the energy source and the signal from the tooth being transmitted through a single window. Optionally, the probe body may include a reflective surface which can be oriented so as to reflect light energy transmitted from the window in which passes through the tooth back toward the window. In other embodiments, the signal may instead rely on light scattering within the tooth.

In yet another aspect, the invention provides an oral health measurement system for measurements of oral health within a mouth of a patient. The mouth has oral surfaces, and the measurement system comprises a measurement apparatus having a visible or non-visible light source. The measurement apparatus also has an electromagnetic signal receiver coupled to a processor. A detachable probe body includes a casing, a surface oriented to engage one or more oral surfaces and at least one window. The casing removably receives the signal receiver and the surface maintains alignment between the signal receiver and the oral object. The at least one window is disposed along an energy path extending from the source to the oral object and from the oral object to the receiver. The at least one window transmits visible or non-visible light energy from the source to the oral object and an electromagnetic signal from the oral object to the signal receiver.

The measurement apparatus will often include at least one of a spectrophotometer, a pulse oximeter, and a laser Doppler system. For example, the electromagnetic source may comprise a laser or light emitting diode (LED) generating light at a first frequency. A blood flow measurement system may include a pulse oximeter module that produces blood oxygenation signals in response to light at the first frequency and light at a second frequency. Optionally, a laser Doppler module may produce blood flow signals in response to light at the first frequency. The detachable probe body may comprise at least one mirror disposed along the optical path. The mirror, for example, may be disposed between an end of a light waveguide and a window, with the light waveguide acting as an energy transmitter, a signal receiver, or both.

The energy source may generate visible or non-visible light energy at a plurality of frequencies, and the measurement apparatus may comprise a spectrophotometer employing at least one of the frequencies, a pulse oximeter employing at least two of the frequencies, and a laser Doppler system employing at least one of the frequencies.

The casing may isolate the signal receiver from the mouth. The processor may determine a health characteristic of the oral object in response to the light signal. The light signal may be modulated per a modulation sequence. The processor may use the modulation sequence to determine the oral health characteristic, the modulation sequence may be random, pseudo-random, or the like, and use of such modulation may improve signal-to-noise performance of the system.

The light source may generate light at a range of frequencies. The processor may comprise a spectrophotometer module for determining the oral health characteristic from the light signal. In addition to blood characteristics, such spectrophotometer capabilities may allow the system to identify the presence or absence of bacteria, bacterial products and the like.

The various aspects of the present invention may make use of detachable probe bodies having outer surfaces which are defined by sterilizable materials. The probe body may be configured for repeated attachment to, and detachment from other system components. Alternatively, the detachable probe bodies may not be safely sterilizable.

In a method aspect, the invention provides a method for measuring oral object health. The method comprises covering a signal receiver with a detachable probe body. The signal receiver is affixed relative to an oral object using the probe-body. An oral health characteristic signal is generated by directing visible or non-visible light energy toward the oral object. The oral object health signal is detected with the affixed signal receiver through a window of the probe body. An oral health characteristic is determined by processing the detected oral health signal with a processor coupled to the signal receiver.

The probe body will often be removed from the mouth and the signal receiver removed from the probe body so that the probe body can be disposed of. The signal receiver may be covered by another probe body, and affixed relative to another oral object in another mouth with the other probe body so as to avoid contamination of the other mouth when reusing the signal receiver. Optionally, removing the signal receiver from the probe body changes the probe body so as to inhibit reuse of the probe body. In other embodiments, the method may comprise removing the signal receiver from the probe body, sterilizing the probe body, recovering the signal receiver with the probe body, and determining a health characteristic of another oral object in another mouth using the same probe body.

DETAILED DESCRIPTION OF THE INVENTION

The present invention generally provides improved devices, systems, and methods for diagnosing bone, tissues, and/or fluids accessible within the oral cavity. In many embodiments, the invention provides improved devices, systems, and methods for determining oral object health, generally through the use of a detachable probe body which allows transmission of electromagnetic energy while protecting fixed or reusable components from contamination, thereby eliminating any need to rely on repeated sterilization of those fixed or reusable components.

While the exemplary embodiments are often described with reference to tooth health measurements, and particularly with reference to tooth vitality measurements, the techniques of the present invention may find applications in diagnosing a variety of diseases of tissues within the oral cavity. For example, along with detecting blood flow and/or oxygenation so as to determine tooth vitality and/or health of gum tissues, the tongue, and dental pulp; the devices, systems, and methods described herein may detect and/or measure disease states using spectrophotometry or other techniques, often employing visible and/or non-visible light energy (including infrared, ultraviolet, and the like), and by detecting and/or measuring signals generated by oral objects in response to that light. Hence, the oral objects to be evaluated may include, but are not limited to teeth, gums, cheeks, and the tongue. Both the electromagnetic energy directed at these oral objects and the signals generated therefrom will often (but not always) be in the form of visible or near-visible light.

In many cases health may be evaluated by determining the quality of blood and its flow within the oral object. However, general evaluation characteristics include, and are not limited to, the presence or absence of any materials, chemicals, biomaterials, bacteria, materials absorbed or secreted by bacteria, the presence or absence of cancerous tissues, or the like. Therefore, the method in the present invention can be used to determine many kinds of health and vitality issues, including vitality and health of a nerve and the pulp within a tooth, decay, the presence of tumors, and the like.

Figure 1:
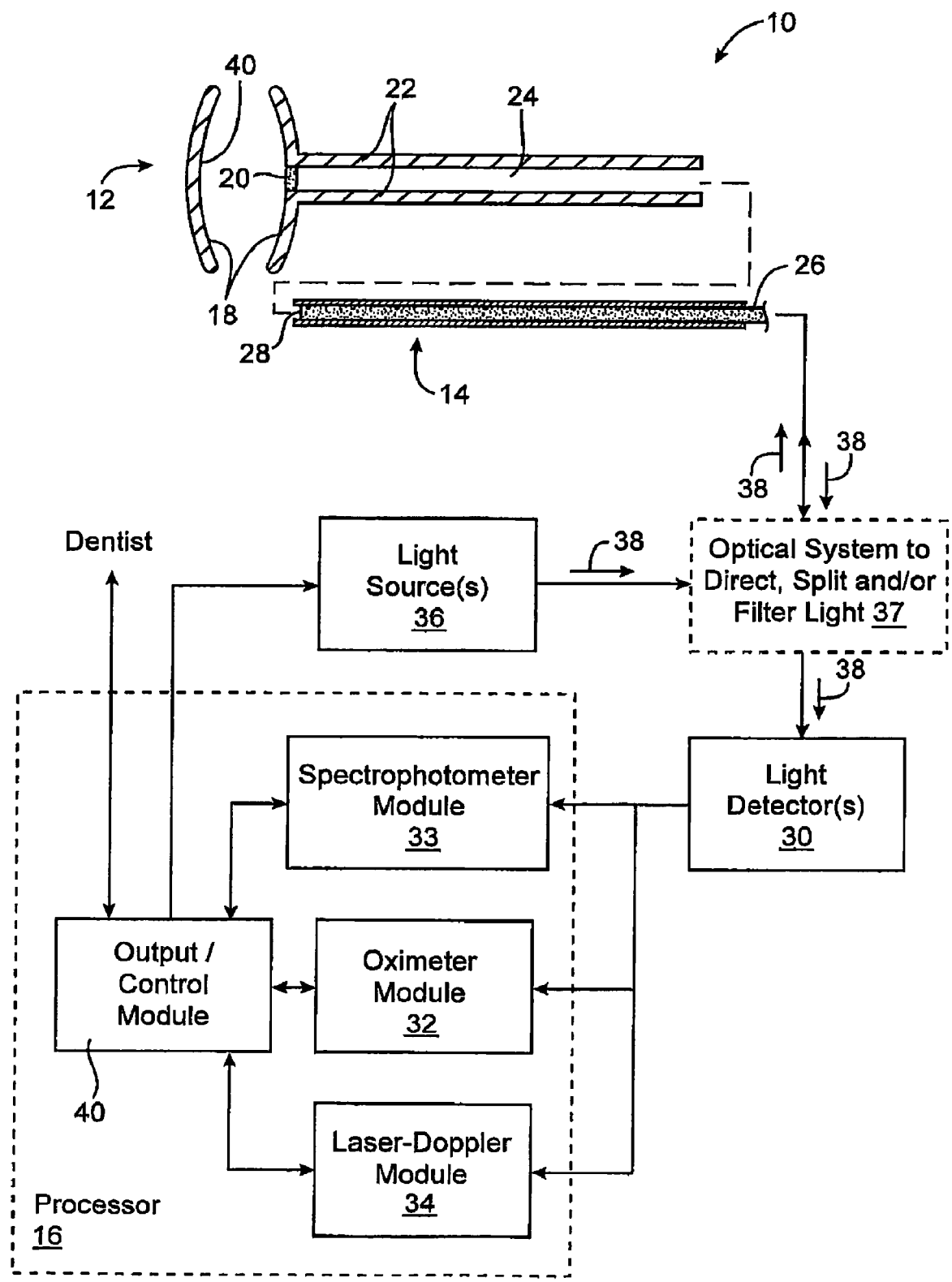
FIG. 1 is a schematic block diagram illustrating an oral object vitality measurement system using pulse oximetry, spectrophotometry, and laser Doppler techniques to measure oral object health, including a detachable probe body configured to maintain alignment of the system components with a tooth or other oral object while providing sterile isolation of the mouth from the reusable system components.

Referring now to FIG. 1, an oral health measurement system 10 generally includes a detachable probe 12 and a reusable signal receiver and transmission medium assembly 14 coupled to a processor 16 so as to allow health measurements of an oral object, for instance of a tooth engaged by the probe.

Figure 2:
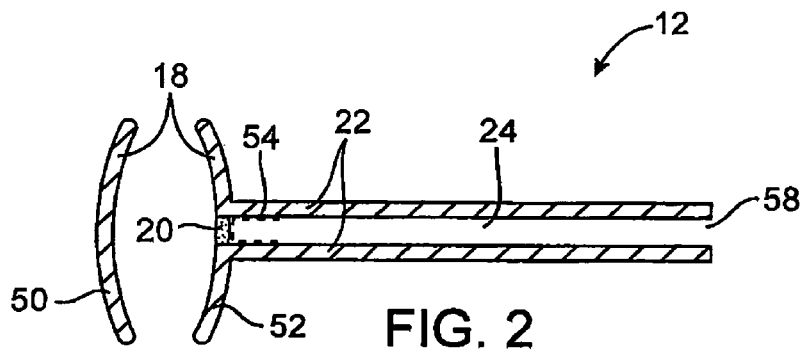
FIG. 2 is a schematic cross sectional image illustrating a detachable probe body for use in the system of FIG. 1.

As can generally be understood with reference to FIGS. 1 and 2, probe 12 includes one or more surface regions 18 which are configured and oriented for engaging one or more surfaces of a tooth or other tissue structure within the oral cavity. Alternative embodiments may engage surfaces of a plurality of oral objects, such as of a plurality of teeth, of a tooth and adjacent gums, and the like. A window 20 is transmissive of electromagnetic signals, typically being transmissive of light signals and light energy. A casing 22 of probe body 12 extends from window 20, with the casing and window together defining an opening 24.

Opening 24 is generally configured to receive a signal receiver and at least a portion of a transmission medium of receiver/medium assembly 14. The exemplary reusable receiver/medium assembly 14 includes an optical waveguide 26 defining a proximal orientation and a distal orientation, with a distal light receiving waveguide end 28.

Optical waveguide 26 directs signals from waveguide end 28 to one or more light detectors 30. An optical system 37 may optionally be provided to direct light energy from a light source 36 toward an oral object and/or signals from waveguide end 28 toward detector 30. Optical system 37 may also split and/or filter light energy and signals, often using known components for splitting, filtering, diffraction, reflection, mixing, and/or other optical operations. Light detector 30 generates electrical signals in response to the light signals, and transmits those electrical signals to processor 16. Processor 16 then uses these electrical signals to determine the vitality and/or other health characteristics of the tooth or other oral object.

Referring still to FIGS. 1 and 2, processor 16 may include, for example, a pulse oximeter module 32, a spectrophometer module 33, and/or a laser Doppler module 34. Pulse oximetry, spectrophotometry, and laser Doppler systems make use of a light source 36 to direct electromagnetic energy toward an oral object so as to induce the oral object to generate a health characteristic signal. In the embodiment of FIG. 1, light source 36 transmits light energy along an optical path 38 through optical waveguide 26, past waveguide end 28, and through window 20 to a tooth. The light may be reflected by a reflective surface 40 of probe body 12 so as to pass twice through an engaged tooth, or may be scattered from within the tooth. Regardless, light signals generated by the tooth in response to the light energy from light source 36 are transmitted proximally through window 20 and end 28, along optical waveguide 26, and to light detector 30 so as to complete the optical path 38.

Processor 16 may comprise a general-purpose computer (such as a desktop computer or a notebook computer) or a specialized computing device. The processor will often include an output device, along with at least one user input device, such as a keypad, keyboard, touch screen, mouse, joystick, or the like. Processor 16 may output the oral health measurement analysis results to the user directly via a screen, light emitting diode, Internet, intranet, or the like, or may record measurement results to magnetic recording media, optical recording media, printed paper, or the like. Processor 16 will also typically include an interface for coupling the processor to light source 36 and light detector 30, the processor, light source, light detector, and/or an associated optical system 37, optionally including optical elements such as mirrors, semitransparent mirrors, filters, prisms, etc., and one or more digital-to-analog converter or the like. Regardless of whether a general purpose computer or specialized device is provided, light source 36 and/or light detector 30 may be mounted within a housing of the processor, may be included in one or more external peripheral devices, or may be insertable at least in part into probe body 12.

System 10 may advantageously make use of any of a large number of widely available components. For example, in an exemplary embodiment, processor 16 and/or output/control module 40 may comprise a suitable SRAM or other memory available from ST Microelectronics or a wide variety of suppliers; a 1M×16 Flash memory available from Intel under model number TE28F160C3BD70; and a micro-controller available from Cypress under model number CY8C27466 PSOC. Processor 16 may also comprise, for example, a DSP available from Motorola under model number DSP56F807, which may also contain (or be used as at least a part of) oximeter module 32, spectrophotometer module 33, and/or laser-Doppler module 34.

An exemplary light source 36 may include, for example, a Lasermate VCSEL source for 650 nm light (such as those found in DVD ROM pickups) available under model number LD-650-7A. As noted above, light source 36 may provide light at a plurality of wavelengths, so that the light source will often include a plurality of light generators, optionally including an array of light generators at one or more frequencies. For example, light source 36 may also include a VCSEL source to generate 850 nm light such as that available from Lasermate under model number LD-850-10A. Three or more different frequencies of light energy may be employed by the system in measuring the health of oral objects, with the exemplary embodiment of light source 36 also comprising a Lasermate FP laser Diode source to generate 1310 nm light commercially available under model number T13F-RFC2-B2. In some embodiments, light source 36 may comprise a source of broadband or white light to provide light through out a range of frequencies, such as a tungsten, deuterium, and/or xenon flash lamp.

An exemplary light detector 30 may similarly include commercially available components, such as a Cypress microcontroller described above, and/or a Pin diode detector available commercially from Lasermate under model numbers RSC-M13P406, RSC-M85P406 and/or RSC-M65P406. Once again, one or more individual light sensitive devices may be employed by light detector 30. Optical system 37 may optionally include any of a wide variety of optical components, such as mirrors, semitranslucent mirrors, lenses, prisms, optical filters, and the like. Processor 16 and/or system 10 may also include, for example, a USB interface such as that available from Cypress under model number CY7C67300.

In some embodiments, system 10 may comprise a handheld system. In such embodiments, processor 16 may comprise a relatively simple controller or processor, such as those embedded in an FPGA. For instance, one or more processors and microcontrollers such as those of a Xilinx FPGA may be readily available and may be suitable for use in a handheld system 10. Suitable handheld processors may include a Pico-Blaze(TM)8-bit microcontroller, a MicroBlaze(TM), a "lightweight" PowerPC, and/or a PowerPC 405. These and other structures may be available commercially through Xilinx. Similarly, Altera offers various processors that may be usable, including the Nios and Nios II family processors. ARM, MIPS, ARC processors, the Hitachi SH-3 and higher series, might be used, as well as historical processors now in the public domain, such as the 8051.

The specific components listed above are examples of structures which may be considered for use in an exemplary system 10, although a large number of alternative components might also be employed. In many alternative systems, some or all of the structures and functions schematically illustrated can be combined or even omitted, so that some systems may have little or no optical system 37, for example. Some system may rely entirely on spectrophotometry (foregoing the use of laser-Doppler 34 and oximeter module 32), while others may employ only pulse oximetry or laser-Doppler, while still others employ a combination of any two of these three alternatives, optionally in combination with one or more additional separate oral health measurement techniques.

In general, processor 16 may include a combination of hardware and software, and will often include machine-readable code embodying computer programming instructions to perform one or more of the method steps described herein. While the various method steps and structures are described and illustrated as being performed by modules, it should be recognized that the functional programming instructions steps of these modules may be integrated into a single programming code, or may be separated into several different codes or subroutines in a wide variety of program code architectures. Similarly, while the schematic illustration of FIG. 1 shows separate modules for pulse oximetry, spectrophotometry, and laser Doppler processing, the actual calculations may be performed by a single integrated module, by separate processor boards, or by a plurality of electronic circuits performing different portions of these calculations for different modules in any of a wide variety of data processing architectures.

Pulse oximeter module 32 takes advantage of changes in blood color with varying oxygenation of the hemoglobin in red blood cells of the blood. Oxygenated blood is bright red, while blood which is lower in oxygen becomes gradually darker in color, bordering on purple. The degree of oxygen saturation can be determined from the color of blood. By directing, for example, a red light through a vascular bed (such as a healthy dental pulp) and measuring how much of the red light is absorbed, pulse oximeters can determine whether blood oxygen saturation is relatively high (thereby absorbing a relatively large amount of red light) or low (from relatively low red light energy absorption).

A number of factors may affect the quantity of red light absorption, including tooth thickness, variations in tooth enamel, tooth color, thickness and location of the dental pulp, the presence of pulp, the presence of any fillings or caps on the tooth, and the like. To accurately compensate for these and other factors, pulse oximeters module 32 may make use of a different light energy generated by light source 36 at a different frequency, such as an infrared light energy. Light detector 30 can measure the strength of the light signals from the oral object at the frequencies of the selectively absorbed red light and at the infrared light frequency. Extraneous light attenuation can thereby be compensated for, allowing accurate determination of red light absorption by the blood which is relatively unaffected by object-to-object variations.

A healthy oral object may include both arterial blood and venous blood. Blood within a vein may tend to be low in oxygen saturation even when the object is healthy, as that blood has already been used to supply the tissue with oxygen and the like. For this reason, it may be advantageous to selectively measure arterial blood. Pulse oximeter module 32 may take advantage of the pulsatile nature of arterial blood flow so as to distinguish arterial blood signals from venous blood signals, as venous blood flow tends to be steadier in nature. By selectively measuring the differences in red light absorption between high and low points of pulse fluctuations (systolic as opposed to diastolic), pulse oximeter module 32 can compensate for the light absorbing effects of steady venous flow and selectively measure color of pulsating arterial blood. In other words, oxygen saturation $SpO_2$ is a function $f$ of the variation between minimum and maximum red light absorption and minimum and maximum infrared light absorption according to the following equation:

$$SpO_2 = f\left[\frac{\ln\left(\frac{\min}{\max}\right)\text{Red}}{\ln\left(\frac{\min}{\max}\right)\text{IR}}\right]$$

Pulse oximeter systems and components are produced by (and may be commercially available from) a number of manufacturers, with existing systems often being intended for use in hospitals. Hospital uses may include anesthesia and neonatology, where monitoring the oxygenation level of blood is of particular benefit. Neurological applications and cerebral oximeter structures may also be employed. Commercially available portable pulse oximeters may be as light as 2 ounces, and the majority of oximeters, whether portable or for desktop use, make use of a probe configured to engage a finger, an earlobe or the nose of a patient. While oximeters may have historically had significant capital investments costs, one or more companies may have introduced portable finger oximeters with much more reasonable costs and good quality. Commercial sources for pulse oximeters include NONIN, BCI, CSI, MASIMO of Irvine Calif., SOMANETICS, INVACARE, NELLCOR of Pleasanton Calif., NOVAMETRIX, SENSORMEDICS, CRITICARE, INVACARE, and RESPIRONICS, MINOLTA of Japan, NIHON KOHDEN of Japan, and OMRON of Japan, as well as from a number of European companies. Pulse oximeter manufacturers have directed significant efforts toward data-logging capability. It can be particularly advantageous in pulse oximetry measurements to avoid and/or overcome measurement problems associated with motion of the patient or of the probe cable. A pulse oximeter with motion detection for modification and use in system 10 is described in U.S. Patent Publication No. US 2004/0034293 in the name of Victor E. Kimball, as published on Feb. 19, 2004, the full disclosure of which is also incorporated herein by reference.

Regarding spectrophotometry module 33, oximetry may be considered part of a wider technology called spectrophotometry. While oximeters measure the reflectance or absorption of two specific colors in order to determine oxygen contents of blood, spectrophotometers may (in some embodiments) more generally measure a range of colors, optionally including the whole visible spectrum and infrared and/or ultraviolet. Depending on the width of the spectrum and the color resolution, a wealth of information can be obtained from an oral object engaged by probe body 12. Hence, spectrophotometers may be used for oximetry, although pulse oximetry may not necessarily provide full spectrophotometric measurements. Spectrophotometers and components thereof may be available from HP, Agilent, Milton Roy, Perkin-Elmer, Varian-Cary, Beckmann Coulter, Amersham Biosciences (part of GE), and Instrument Systems GmbH.

Laser Doppler module 34 may similarly make use of light energy transmitted to the tooth from light source 36. In the case of laser Doppler measurements, the light may be readily directed from end 28 and through window 20 to the tooth so as to be scattered within the tooth. Light scattered from within the dental pulp and other structures of the tooth can be transmitted proximally through window 20 and end 28 to light detector 30 along optical path 38 as described above. Laser Doppler module 34 will typically employ measurements of light signal frequencies generated by the tooth in response to monochromatic light from light source 36.

In laser Doppler measurements monochromatic light will often be absorbed and scattered within the oral object. Part of the light is scattered by a static oral object, while another part of the monochromatic light will be scattered by moving blood cells within the oral object. The light scattered by the moving cells undergoes a slight frequency shift due to the Doppler effect. The mixing of the Doppler shifted and unshifted back-scattered light as measured by a light detector 30 will include intensity fluctuations with Doppler frequencies. The Doppler signal can be determined by the number of red blood cells and their velocities in the oral object, and may give rise to, for example, Doppler frequency components in a range of up to 50 kHz. Processing of electrical signals from light detector 30 within laser Doppler module 34 throughout a range of 0-50 kHz can thereby provide a measurement of blood flow within the oral object.

Control module 40 may modulate the light generated by light source(s) 36 (e.g., by pulsing, amplitude variation or frequency modulation) to enhance the processing capabilities and/or performance, and particularly the signal-to-noise performance of modules 32, 33, and 34. Said modules could for instance contain synchronous detectors, the use of which may reduce steady state interferences. Modulation may allow measurement of characteristics that are undetectable or more difficult to measure with an un-modulated light source.

An output/control module 40 of processor 16 may supervise generation of the light energy by light source 36. Once again, there are a number of commercial sources and manufacturers of laser-Doppler systems and devices, including Perimed AB, of Sweden, Moor Instruments Ltd. of the United Kingdom, Oxford Optronix of the United Kingdom, Transonic Systems Inc. of the United States, and the like. Output/control module 40 may also correlate pulse oximetry, spectrophotometry, and/or laser Doppler blood flow measurements from modules 32, 33, and/or 34 so as to provide an output signal to the system user indicating the measured health of the oral object. The output will generally comprise a readout of oral object health, as indicated by the measurement results. For example, in the case of tooth vitality measurements, tooth vitality as indicated by blood flow and/or blood oxygen within the dental pulp may be output, thereby providing an objective tooth vitality indication. The output may indicate oxygen saturation and/or blood flow speed or quantity, as well as indicating the vitality of the tooth to the system user.

Light source 36 will often comprise one or more light emitting diodes, laser diodes, bandpass filtered broad-band light sources, unfiltered broadband light sources, or the like, and may produce light energy at one frequency or a plurality of different frequencies. In some embodiments, a plurality and/or an array of light sources may be used, and any of a variety of known optical components such as lenses, filters, prisms, and the like may be included in the optical path. Light detector 30 may comprise an electrooptical sensor or light receiver, an array of sensors, or the like. The light source may optionally provide (for example) light of about 660 nm and infrared light of 850 nm, and light detector 30 may measure light intensity at one or more such frequencies. Light detector 30 may also measure laser Doppler frequencies from the light source frequencies, and will often include one or more photodetector semiconductor chips.

Figure 3A:
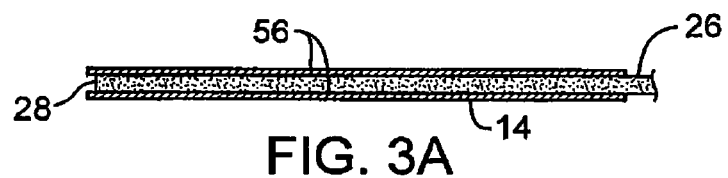
FIGS. 3A and 3B are schematic cross sections illustrating alternative light transmitting and receiving structures and associated transmission media for use in the detachable probe body of FIG. 2.
Figure 3B:

Referring now to FIGS. 2, 3A, and 3B, the structure and interaction between probe body 12, alternative transmission media, and alternative signal receivers can be understood. Probe body 12 includes a first probe body portion 50 having a first tooth engaging surface 18 and a second probe body portion 52 having a second tooth engaging surface. The probe body portions can move relative to each other, thereby forming a clamp for affixing probe body 12 relative to a tooth, gums, or other oral objects. Probe body 12 also defines a receptacle 54 which fittingly receives signal receiver/transmission media assembly 14, thereby affixing the signal receiver (waveguide end 28 in this embodiment) relative to the tooth. Window 20 may sealingly engage the adjacent portions of casing 22 and/or first and second portions 50, 52 so as to maintain sterile isolation of the signal receiver and adjacent transmission media from the mouth.

In some embodiments, the window and adjacent portions of the probe body may comprise the same material, and/or may be integrally formed. In other embodiments, window 20 may be bonded to the adjacent structures of the probe body using adhesives, ultrasonic welding, or the like. For example, window 20 may comprise a transmissive structure integrally formed with adjacent portion 52 and aligned with the signal receiver, or may comprise a transmissive structure formed as a portion of adjacent casing 22 and aligned with the signal receiver. Suitable materials for fabrication of window 20 include, for example, polycarbonate, glass, and/or mica. Optionally, window 20 may comprise a lens to focus or defocus the electromagnetic signal from the oral object onto the signal receiver. Alternatively, window 20 may transmit the signal unaltered.

The first and second portions, 50, 52 and casing 22 of probe body 12 may comprise a material such as polysulfone, acetal, nylon, and/or ABS plastic. The first and second portions may be affixed to casing 22 by bonding, fasteners, adhesives, ultrasonic welding, a threaded connection, or the like, or these structures may be formed integrally by molding these parts (or all of) probe body 12 as a single piece, for example. Standard injection molding processes may be used to fabricate the probe body as portions, whether they are formed separately or as one or more integral units.

Optical waveguide 26 of signal receiver/energy transmitter 14 may comprise a single fiber or a bundle having two or more fibers, with fibers often comprising glass optical fibers. An insertable portion 56 is generally adapted for insertion into opening 24 of probe body 12, insertable piece 56 may, for example, comprise a surgical steel tube having an inner diameter such that a bundle of glass fibers is encased and held firmly thereby. An outer diameter of insertable piece 56 may fittingly engage the surrounding casing 22 of probe body 12 when signal receiver/transmitter 14 is inserted therein. A proximal end 58 of casing 22 may be separated from window 20 by a distance sufficient so that the proximal end is disposed outside the oral cavity when probe body 12 is in use.

In the embodiment of FIG. 3B, insertable piece 56 supports one or more electro-optical light sensors or photodetectors 60. Photodetector 60 comprises a light receiving sensor which generates electrical signals in response to light, and may be mounted to a substrate with or without related electronic circuitry and electrical wires. Optionally, photodetector 60 may comprise an array of sensors, and the electrical signals from the photodetector may vary with a strength of the light signals from the oral object, with a frequency of the light signals from the oral object, and/or the like. The substrate of the photosensor may also support a light source such as a light emitting diode (LED), a laser diode, or the like, or a separate substrate may be provided with or without related electronic circuitry and/or electrical wires. The light source or an array of light sources may be included within insertable piece 56. Electrical wires 62 couple the photodetector 60 to processor 16, and thereby serve as a transmission medium. Hence, in the embodiment of FIG. 3B, light source 36 and/or light detector 30 are incorporated into insertable piece 56 for insertion into probe body 12.

To enhance performance of the system, the signal receiver (whether in the form of an optical fiber end 28 or a photodetector 60 or some other light signal receiving structure) may include one or more lenses (such as GRaded INdex or GRIN lenses, spherical lenses, or the like), non-reflective coatings, and/or the like. In other embodiments, a wireless transponder may be coupled to a photodetector and inserted into opening 24 of probe body 12, so that the transponder acts as a signal transmitter without relying on optical cables, wires, or the like, and so that the casing 22 need not extend out of the mouth. Energy for such a transponder may be provided by a battery disposed within opening 24, or energy may be supplied from an external electromagnetic field, the wireless transponder optionally conveying information by dynamically changing the active load of the external electromagnetic field.

In the embodiment of FIG. 2, light may be transmitted toward the oral object through window 20, and may also be received from the oral object through window 20. As can be understood with reference to FIG. 4, alternative embodiments may include first and second windows 20a, 20b positioned so as to transmit light through the tooth (or other oral object) therebetween. Pulse oximeter systems may benefit from probe structures which are configured to transmit light through an oral object such as a dental pulp, while laser Doppler devices are particularly well suited to transmitting light to and receiving scattered light from the oral object from one side of the oral object, and can be easily used with or without transmitting the light through the oral object. Nonetheless, pulse oximetry, spectrophotometry, and laser Doppler techniques may be used by transmitting light through the oral object, and/or using arrangements in which light is transmitted and received through a single window, adjacent windows, or the like.

Figure 4:
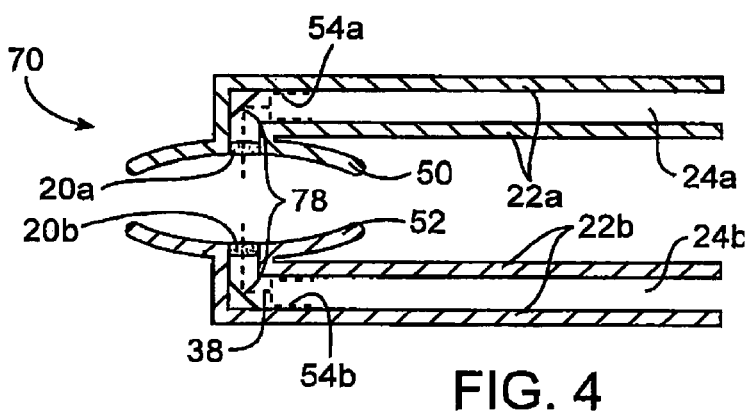
FIG. 4 is a schematic cross section illustrating an alternative detachable probe body for use in the system of FIG. 1.
Figure 5A:
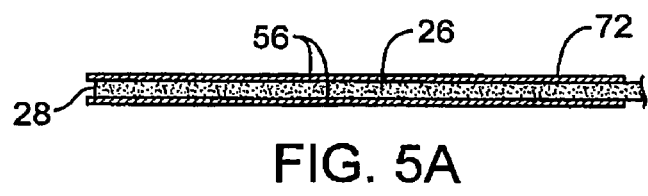
FIGS. 5A and 5B are schematic cross sections illustrating a light waveguide and a light detecting or generating circuit for use together in the detachable probe of FIG. 4, optionally using two separate light waveguides, two separate circuits, and associated conductors or one waveguide and one circuit conductor set for transmitting energy to an oral object and passing signals from the oral object to a processor.
Figure 5B:

Referring now to FIGS. 4, 5A, and 5B, pass-through probe body 70 includes first and second portions 50, 52 which move relative to each other and to clamp a tooth therebetween. First and second windows 20a, 20b are disposed along optical path 38 between first and second receptacles 54a, 54b, first and second casings 22a, 22b define first and second openings 24a, 24b, respectively. An optical waveguide insertable portion 72 includes a waveguide end 28 which may be used for sending optical energy toward the oral object or receiving optical signals from the oral object. An electro-optical insertable portion 74 includes an electro-optical device 76 which likewise can either send energy or receive optical signals. Pass-through probe body 70 may make use of electrical energy transmitted from a fiberoptic cable or an electro-optical device (such as a laser diode) disposed within first opening 24a. Similarly, pass-through probe body 70 may make use of signals received by an end of an optical waveguide 28 and transmitted by the optical waveguide 26, or signals received by an electro-optical device (such as a photodetector) and transmitted by wires 62 from within second opening 24b.

Openings 24a, 24b extend along an adjacent surface of a tooth, so that distal ends of the signal transmitting and receiving structures are not normal to the tooth surface. So as to enhance efficiency and provide a more comfortable probe, mirrors 78 directs optical path 38 between the energy transmitter and signal receiver. Receptacles 54a and/or 54b may be defined, for example, by surrounding casings 22a, 22b and by a feature of pass-through probe body 70 engageable with the distal end of the insertable piece, such as a surface of mirror 78. To allow the casing and insertable piece to move to a comfortable position clear of other oral tissues, a joint may be provided between the casing 22a, 22b and the adjacent portions 50, 52, with the joint optionally comprising a rotational joint allowing rotation about an axis of optical path 38.

Figure 6A:
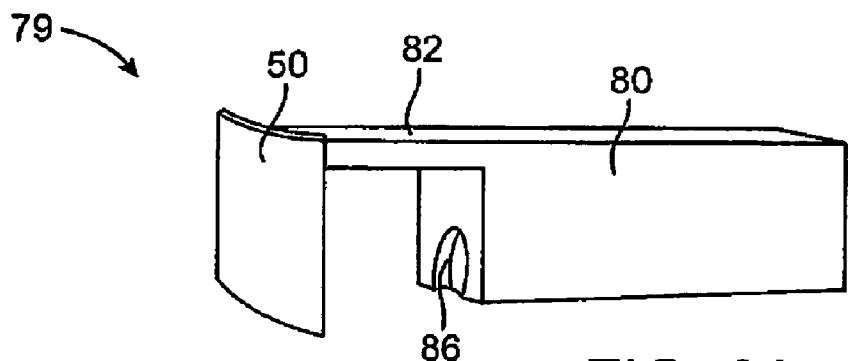
FIGS. 6A through 6C are simplified perspective views schematically illustrating components of a detachable probe body and associated light receiving and transmitting components for use in the system of FIG. 1.
Figure 6B:
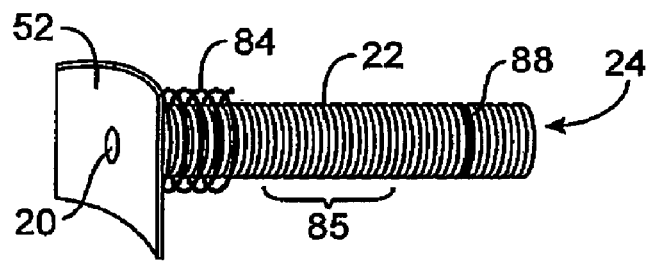
Figure 6C:
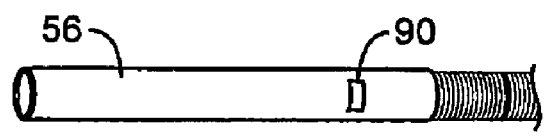
Figure 7:
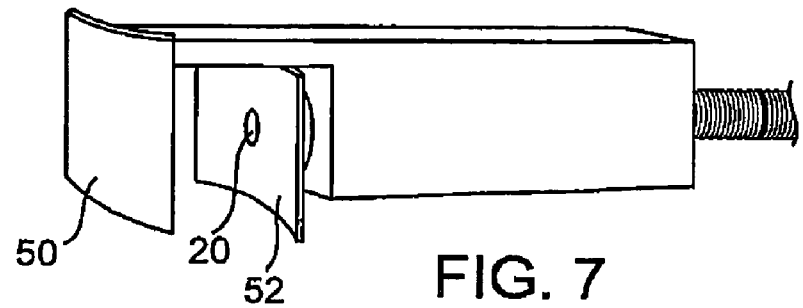
FIG. 7 is a perspective view illustrating the assembled components of FIGS. 6A-C.

Referring now to FIGS. 6A-7, additional details on a clamp structure for securing a probe body to a tooth, adjacent gum, or other tissue surfaces within the mouth can be understood. In this embodiment of a clamp probe body 79, first portion 50 is supported relative to a housing 80 by an arm 82. Second portion 52 with window 20 and the adjacent casing 22 are biased by a spring 84 when casing 22 is movably disposed within a channel 86 of housing 80. As a result, second portion 52 (and the light transmitting/receiving structure) are urged toward first portion 50 so as to clamp a tooth therebetween.

As can be understood with reference to FIGS. 6B and 6C, a feature such as an indented portion 88 of the probe may engage with a corresponding surface of a re-usable component. In this embodiment, indented portion 88 protrudes into a detent 90 of insertable portion 56 when the light transmitter or receiver is disposed at the receptacle adjacent window 20. The engaging surfaces of indentation 88 and detent 90, together with the adjacent structure, may be configured so as to impose changes on the probe body when the insertable portion is removed therefrom to inhibit re-use of the probe body. For example, casing 22 may be frangible adjacent indentation 88 such that when insertable portion 56 is removed the adjacent casing may be at least in part severed. Alternatively, indented portion 88 may be permanently deformed. Without an appropriate structure to retain the insertable portion adjacent window 20, it may be difficult or impractical to reuse the probe body.

Referring again to FIG. 6B, the first portion may slidingly receive the second portion with a toothed or ratchet mechanism. This ratchet mechanism may allow the second portion to travel towards the first portion, but may inhibit movement of the two parts away from each other until a release mechanism is employed. A toothed portion of 85 of casing 22 is shown in FIG. 6B, and may engage cooperating grooves/teeth inside channel 86 of housing 80.

Figure 6E:
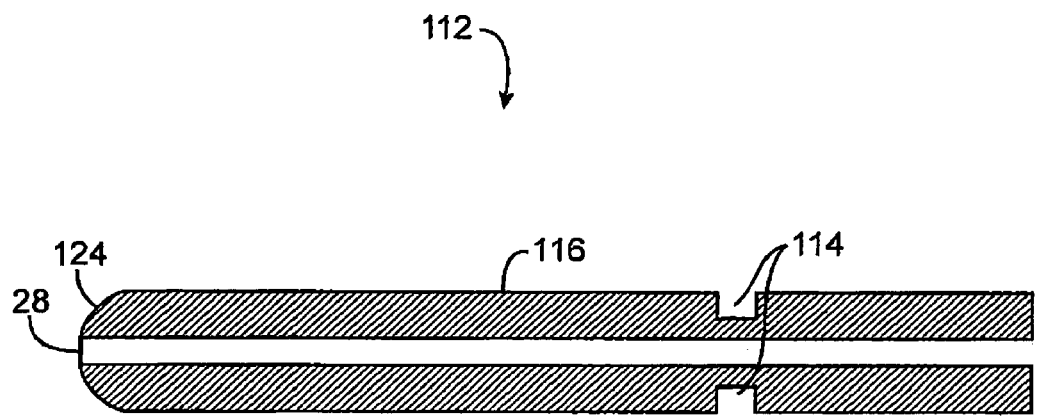
FIGS. 6D and 6E are schematic cross-sections showing a frangible embodiment of the probe body and associated reusable components.
Figure 6D:
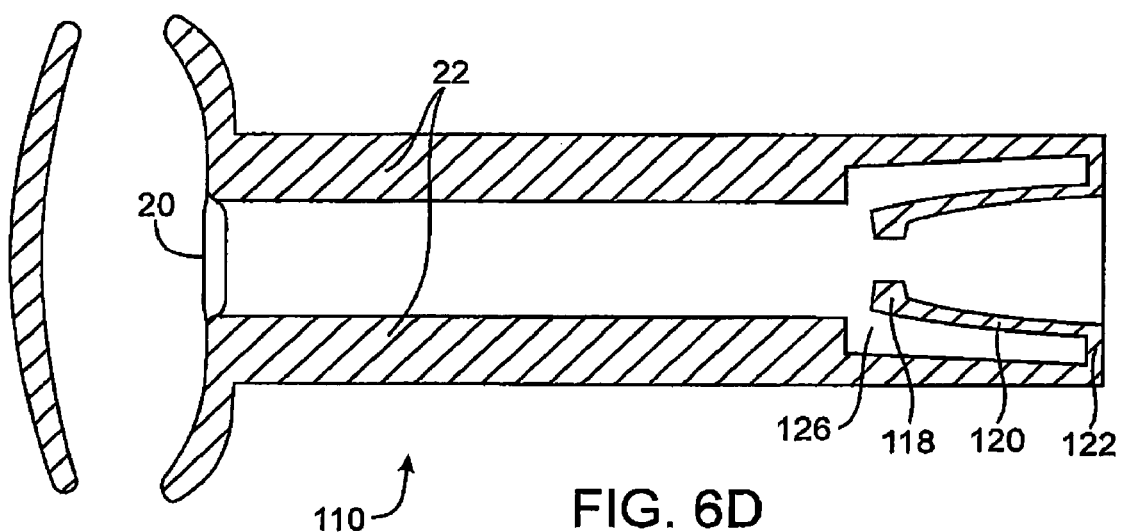

A wide variety of alternative structures might be used. Optionally, a ratchet clamp structure might be employed with removal effected by releasing the ratchet. An exemplary frangible probe body 110 and associated intra-oral reusable components are illustrated in FIGS. 6D and 6E, respectively. The probe body again has a casing 22 as shown in a cross-sectional view. A reusable insertable piece 116 in which the transmission medium 26 is fixed has one or more cuts or grooves 114.

Frangible probe body 110 has one or more detent 118 that fits into groove 114 and that can fix insertable piece 116 (and hence end 28) in a desired locked position relative to window 20. Each detent 118 is coupled to casing 22 by a spring 120, with a breakpoint 122 coupling the spring to the casing. Insertable piece 116 has a rounded point 124, so that upon insertion of the insertable piece into casing 22, detent 118 is pushed into a cavity 126. Once insertable piece 116 is fully inserted, detent 118 is urged into groove 114 by spring 120.

When insertable piece 116 is removed from frangible probe body 110, the detent 118 and spring 120 break from casing 22 at the breaking point 122, such that further use of the probe body is inhibited, as the insertable piece can no longer be fixed into a locked position. Insertable piece 116 is not affected, and can be used with another frangible probe body 110.

Figure 8:
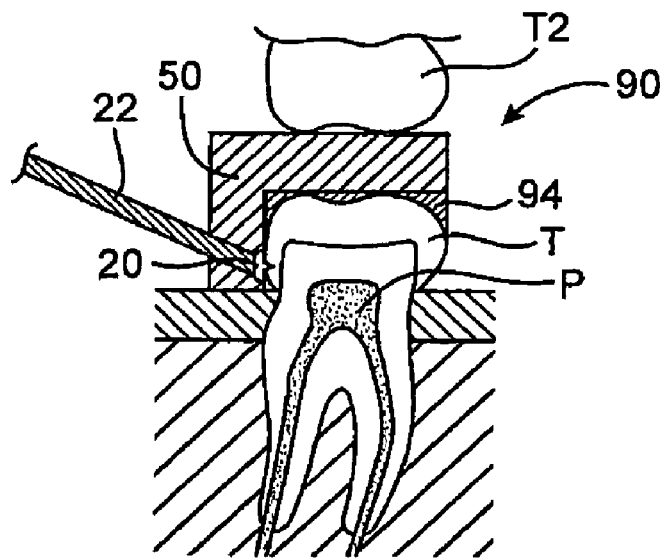
FIG. 8 is a simplified cross section illustrating an alternative detachable probe structure and method for its use in which the probe comprises an adhesive or deformable material to help maintain alignment, and in which the patient bites the probe body to help maintain alignment of the signal receiver with a tooth.
Figure 9:
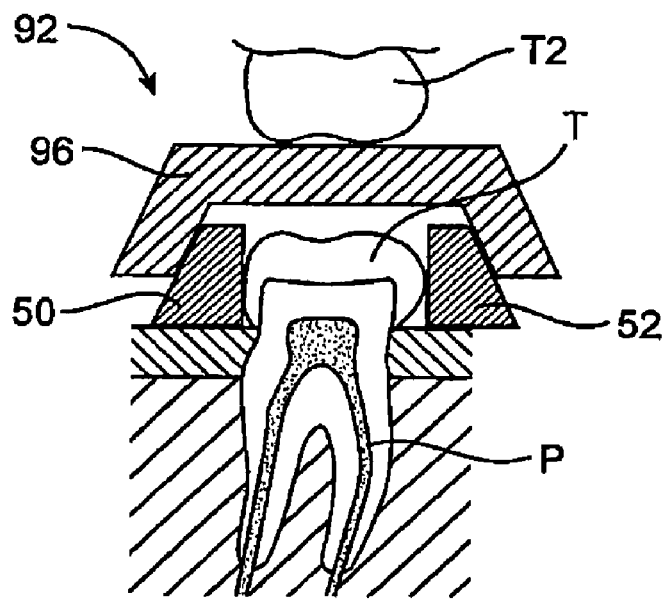
FIG. 9 illustrates a further alternative detachable probe body in which the patient bites the probe body so as to clamp the probe body onto the tooth and maintain alignment.

As can be understood with reference to FIGS. 8 and 9, a tooth T having pulp P is illustrated while employing the tooth vitality measurement methods of the present invention. In these embodiments, probe bodies 90, 92 are held in alignment with tooth T at least in part by biting of the probe bodies between the tooth and another tooth T2. In the embodiment of FIG. 8, a deformable material 94 introduces lateral friction or temporarily glues the probe body to tooth T (or another oral object). Suitable deformable materials might include thixotropic gels, such as polyvinyl siloxane (sold commercially as Star VPS™). In the embodiment of FIG. 9, first and second portions 50, 52 of probe body 92 are squeezed together by biting down on a third portion 96 having a wedge-shaped inner surface. This squeezes the first and second portions 50, 52 towards each other on opposed surfaces of tooth T.

A variety of additional embodiments and variations are also possible. In general, the casing may comprise a rigid or semi-rigid structure. In many embodiments, the casing will extend so that the signal receiver, energy transmitter, and at least a portion of the signal transmission medium (and/or wireless signal telemetry components) are covered by the casing or otherwise need not touch any oral objects or be exposed to the oral cavity when the probe body is positioned in situ. In some embodiments, at least a portion of the probe body may comprise a flexible or deformable structure. For example, casing 22 may be sufficiently long and flexible that the associated components of the system are protected while providing the comfort and safety of allowing the transmission medium to be directed from a variety of positions within the oral cavity. In some embodiments, some or all of the probe body may comprise a highly flexible material such as a membrane or a cloth. A variety of releasable catches may be employed to hold the insertable components of the system within the casing for the course of measurement of a single oral object or multiple oral objects within the patient's mouth. As the probe body may be disposable, the catch or casing may break or be rendered unusable upon release so as to avoid re-use and contamination of a different patient. Alternatively, the probe body may be sterilizable. Flexibility and/or a joint of the casing relative to the oral object engaging surfaces and window of the probe body may accommodate a variety of attachment angles so as to measure vitality of teeth that might otherwise be difficult to access.

Tooth-vitality testing probe bodies, and more generally, probe bodies intended for the oral-object health measurements described herein, may be classified as semicritical devices. Approval and use of such devices may benefit from configuring, marketing, and using the devices as either disposable or sterilizable. Suitable sterilization techniques to apply may include autoclave (steam and pressure for 30 minutes), ultrasonic, and/or cold sterilization (overnight). Hence, the detachable probe bodies will often be either disposable or sterilizable using these or other techniques.

Disposable probe bodies may have frangible and/or permanently deformable structures which are altered by their intended use so as inhibit use with another patient. Circuitry may be mounted to some disposable probe bodies to inhibit re-use in a wide variety of specific schemes. A probe body identifying signal stored on the probe body may be transmitted to the processor of the system so that the processor can inhibit use of that probe body with another patient. Alternatively, an electrical or optical component of the probe body may be irreversibly altered by electrical or optical energy during use, with the system detecting the state of that electrical or optical component before oral health measurements so as to inhibit re-use (and potential cross-contamination) with a different patient. Re-use of a probe body may be inhibited after a single measurement of a single oral object. In other embodiments, re-use may be inhibited in response to alteration of a name of a patient input into the processor, in response to a predetermined number of uses and/or a predetermined time passing since an initial use with a first oral object, or the like, often so as to allow the probe body to be employed for health measurements of a plurality of oral objects in a single mouth of a single patient.

Disposable probe bodies may comprise materials, surfaces, and/or structures which are difficult to effectively sterilize and/or which deteriorate significantly when subjected to sterilization. Such disposable probe bodies may be fabricated at relatively low cost while being comfortable for the patient, as they may be resiliently and/or plastically deformed, bent, formed, or cut to shape. Disposable probe bodies might include, for example, surfaces which are porous (such as those formed as foams), internal cavities, low-temperature thermoplastics (which may not withstand an autoclave), simple adhesive bonds (which may not withstand ultrasound or cold sterilization), and the like. In contrast, sterilizable probe bodies will often be configured of materials, shapes, and/or assembly techniques which can safely and repeatedly withstand the rigors of one or more sterilization techniques without unacceptable deterioration in system performance. Such probe bodies may comprise, for example, glass, metals, higher-cost polymers, threaded and other disassembleable fabrication techniques, and the like. In some embodiments, at least a portion of the probe body (such as the window) may be fabricated as a re-usable and sterilizable component, while another portion (such as a deformable tooth-engaging surface) may comprise a disposable component.

While the exemplary embodiments have been described in some detail for clarity of understanding and by way of example, a number of changes, modifications, and adaptations will be obvious to those with skill in the art. Hence, the scope of the invention is limited solely by the appended claims.

What is claimed is:

1. A detachable probe body for use with an oral health measurement system for oral health measurements of an oral object within a mouth of a patient, the mouth having oral surfaces, the health measurement system having reusable components including an electromagnetic signal receiver coupled to a processor for evaluating a health-related characteristic of the mouth from an electromagnetic signal, the probe body comprising:

a window capable of transmitting the electromagnetic signal from the oral object to the signal receiver;

a casing extending from the window, the casing and window together defining an opening for receiving the signal receiver so as to provide isolation of the reusable components from the mouth; and at least one probe surface oriented to engage one or more oral surfaces so as to maintain alignment between the signal receiver and the oral object.

2. The probe body of claim 1, wherein the at least one probe surface comprises a first probe surface region and a second probe surface region, the probe receiving the oral object with the first and second probe surface regions.

3. The probe body of claim 2, wherein the probe body comprises a first probe body portion having the first probe surface region and a second probe body portion having the second probe surface region, the second body portion movable relative to the first body portion.

4. The probe body of claim 3, further comprising a biasing structure urging the first probe surface region toward the second probe surface region when the oral object is at a desired position there between so as to accommodate a range of differing oral object sizes.

5. The probe body of claim 4, wherein the first portion slidingly receives the second portion, the biasing structure comprising a spring urging the second region toward the first region when the oral object is received there between.

6. The probe body of claim 3, further comprising a ratchet coupling the first probe body portion to the second probe body portion, the ratchet oriented to allow movement of the first probe surface region toward the second probe surface region and to inhibit movement of the first probe surface region away from the second probe surface region.

7. The probe body of claim 3, wherein at least one of the first body portion, the second body portion, and an intermediate portion coupling the first and second body portions comprises a deformable material.

8. The probe body of claim 7, wherein the deformable material resiliently biases the first probe surface region toward the second probe surface region.

9. The probe body of claim 7, wherein the deformable material defines the first probe surface region, the deformable material being sufficiently soft to deform against the oral object when a dentist manually applies pressure.

10. The probe body of claim 5, wherein the first probe body portion is configured to move toward the second body portion when a pressure is applied with an orientation lateral relative to the movement.

11. The probe body of claim 10, wherein the probe body is configured so as to induce the movement of the body portions and engage opposed surfaces of at least one tooth when the patient bites the probe body.

12. The probe body portion of claim 1, wherein the at least one surface is configured to be engaged by the patient biting the probe body.

13. The probe body of claim 1, wherein the at least one probe surface is defined by a material that deforms and introduces friction so as to temporarily affix the probe body relative to the oral object.

14. The probe body of claim 1, the reusable components of the measurement system including a transmission medium or a wireless system, wherein the casing fittingly receives the signal receiver to a predetermined position within the opening, the casing comprising a sheath receiving at least a portion of the transmission medium or the wireless system so as to maintain sterile separation between the reusable components and the mouth.

15. The probe body of claim 14, wherein the transmission medium comprises an optical waveguide and the signal receiver comprises a distal end of the optical waveguide, wherein the sheath distally receives the waveguide.

16. The probe body of claim 15, further comprising a mirror disposed along an optical path between the window and the end of the optical waveguide.

17. The probe body of claim 16, further comprising a joint coupling the sheath to an oral object-receiving portion of the casing so as to allow movement there between.

18. The probe body of claim 1, further comprising a joint coupling at least a portion of the casing to the at least one probe surfaces.

19. The probe body of claim 14, wherein the transmission medium comprises an electrical conductor and the signal receiver comprises a light detector circuit, the sheath receiving a portion of the conductor adjacent the light detector circuit.

20. The probe body of claim 14, wherein the signal receiver of the oral health measurement system is coupled to an electromagnetic source of the oral health measurement system, and the casing receives the signal receiver and electromagnetic source therein.

21. The probe body of claim 14, the casing having a feature for engaging a surface of the oral health measurement system to position the signal receiver relative to the casing.

22. The probe body of claim 21, wherein the casing is frangible or permanently deformable adjacent the feature when the signal receiver is removed from the casing so as to inhibit re-use of the probe body.

23. The probe body of claim 22, further comprising at least one material that is difficult to sterilize.

24. The probe body of claim 1, further comprising at least one material that is difficult to sterilize.

25. The probe body of claim 1, wherein at least an outer surface of the probe body is sterilizable.

26. The probe body of claim 22, the oral health measurement system having a source of visible or non-visible light energy, and further comprising another window and another casing for receiving at least a portion of the energy source of the oral health measurement system.

27. The probe body of claim 1, wherein the oral health measurement system includes a source of visible or non-visible light energy coupled to a transmission medium, the transmission medium also directing the signal from the signal receiver to the processor, the signal receiver comprising an integrated signal receiver/energy transmitter, the opening of the probe body removably receiving at least a portion of the transmission medium adjacent the integrated signal receiver/energy transmitter.

28. The probe body of claim 27, further comprising a reflector, the oral object being disposed between the window and the reflector when the window is oriented to transmit the energy toward the oral object so that the reflector helps direct the energy back through the window and to the integrated signal receiver energy transmitter.

29. A detachable probe body for use with a blood measurement system for tooth vitality measurements of a tooth within a mouth of a patient, the mouth having oral surfaces, the blood measurement system having reusable components including a light signal receiver coupled to a processor for evaluating a characteristic of blood from an electromagnetic signal, the probe body comprising:
  a window capable of transmitting the light signal from the tooth to the signal receiver;
  a casing extending from the window, the casing and window together defining an opening for receiving the signal receiver and at least a portion of a signal transmitter so as to provide isolation of the reusable components from the mouth; and
  at least one surface oriented to engage one or more oral surfaces so as to maintain alignment between the signal receiver and the tooth.

30. The probe body of claim 29, wherein the at least one surface comprises a first probe surface region and a second probe surface region, the probe body receiving the tooth with the first and second surface regions, further comprising a biasing structure urging the first probe surface region toward the second probe surface region when the tooth is at a desired position therebetween so as to accommodate a range of differing teeth.

31. The probe body of claim 29, wherein the probe body comprises a first probe body portion having a first probe surface region and a second probe body portion having a second probe surface region, the first portion slidingly being urged toward the second region of the second portion when the tooth is received therebetween and the patient bites the probe body.

32. The probe body of claim 29, wherein the at least one surface is defined by a material that deforms so as to temporarily affix the probe body relative to the tooth.

33. The probe body of claim 29, wherein the casing fittingly receives the signal receiver to a predetermined position within the opening.

34. The probe body of claim 29, wherein the blood measurement system includes an optical waveguide and the signal receiver comprising a distal end of the optical waveguide, wherein the opening distally receives the waveguide.

35. The probe body of claim 29, wherein the blood measurement system includes an electrical conductor and the signal receiver comprising a light detector circuit, the opening receiving the light detector circuit and at least a portion of the conductor adjacent the light detector circuit.

36. The probe body of claim 29, the casing having a feature for engaging a surface of the blood measurement system to position the signal receiver relative to the casing, the casing being frangible or permanently deformable adjacent the feature when the signal receiver is removed from the casing so as to inhibit reuse of the probe body.

37. The probe body of claim 29, the blood measurement system having a light energy source and an energy transmission medium, and further comprising another window and another casing defining another opening for receiving the energy source and at least a portion of the energy transmission medium.

38. The probe body of claim 29, wherein the blood measurement system includes a light energy source and an energy transmission medium for directing energy to the tooth, the energy transmission medium also directing the signal from the signal receiver to the processor, the signal receiver comprising an integrated signal receiver/energy transmitter, the opening of the probe body receiving at least a portion of the transmission medium adjacent the integrated signal receiver/energy transmitter.

39. An oral health measurement system for measurements of an oral object within a mouth of a patient, the mouth having oral surfaces, the measurement system comprising:
  a measurement apparatus having a visible or non-visible light source, and having an electromagnetic signal receiver coupled to a processor;
  a detachable probe body having:
    a casing removably receiving the signal receiver,
    a surface oriented to engage one or more oral surface so as to maintain alignment between the signal receiver and the oral object, and
    at least one window disposed along a path extending from the source to the oral object and from the oral object to the receiver, the at least one window transmitting visible or non-visible light energy from the source to the oral object, and an optical signal from the oral object to the signal receiver.

40. The oral health measurement system of claim 39, wherein the measurement apparatus comprises at least one of a spectrophotometer, a pulse oximeter, and a laser Doppler system.

41. The oral health measurement system of claim 40, wherein the electromagnetic source comprises a laser or light emitting diode generating light at a first frequency, and wherein a blood flow measurement apparatus includes a pulse oximeter module that produces blood oxygenation signals in response to light at the first frequency and light at a second frequency, and a laser Doppler module that produces blood flow signals in response to light at the first frequency.

42. The oral health measurement system of claim 39, wherein the detachable probe body comprises at least one mirror disposed along the optical path 43. The oral health measurement system of claim 39, wherein the energy source generates visible or non-visible light energy at a plurality of frequencies, and, wherein the measurement apparatus comprises a spectrophotometer employing at least one of the frequencies, a pulse oximeter employing at least two of the frequencies, and a laser Doppler system employing at least one of the frequencies.

44. The oral health measurement system of claim 39, wherein the casing isolates the signal receiver from the mouth, and wherein the processor determines a health characteristic of the oral object in response to the light signal.

45. The oral health measurement system of claim 44, wherein the light source is modulated per a modulation sequence, and wherein the processor uses the modulated sequence to determine the health characteristic.

46. The oral health measurement system of claim 45, wherein the light source generates light at a range of frequencies, and wherein the processor comprises a spectrometer module for determining the oral health characteristic from the light signal.

47. An apparatus as claimed in claims 1, 29, or 39, wherein an outer surface of the probe body is defined by sterilizable material, and wherein the probe body is configurable for repeated attachment to and detachment from other system components.

48. An apparatus as claimed in claims 1, 29, or 39, wherein the probe body is not safely sterilizable.

49. A method of measuring an oral object health, the method comprising:

covering a signal receiver with a detachable probe body;

affixing the signal receiver relative to an oral object with the probe body;

generating an oral object health characteristic signal by directing visible or non-visible light energy toward the oral object;

detecting the oral object health signal with the affixed signal receiver through a window of the probe body;

determining an oral object health characteristic by processing the detected oral object health signal with a processor coupled to the signal receiver.

50. The method of claim 49, further comprising removing the probe body from a mouth, removing the signal receiver from the probe body and disposing of the probe body, covering the signal receiver with another probe body, and affixing the signal receiver relative to another oral object in another mouth with the other probe body so as to avoid contamination of the other mouth when re-using the signal receiver.

51. The method of claim 49, wherein removing the signal receiver from the probe body comprises changing the body so as to inhibit reuse of the probe body.

* * * * *